(12) United States Patent
Sedelmeier et al.

(10) Patent No.: US 7,728,024 B2
(45) Date of Patent: *Jun. 1, 2010

(54) METAL SALTS OF 2'-(1H-TETRAZOL-5YL)-1.1'-BIPHENYL-4-CARBOXALDEHYDE

(75) Inventors: Gottfried Sedelmeier, Schallstadt (DE); Dominique Grimler, Hirsingue (FR)

(73) Assignee: Novartis AG, Basel (CH)

( * ) Notice: Subject to any disclaimer, the term of this patent is extended or adjusted under 35 U.S.C. 154(b) by 134 days.

This patent is subject to a terminal disclaimer.

(21) Appl. No.: 11/995,240

(22) PCT Filed: Jul. 10, 2006

(86) PCT No.: PCT/EP2006/006730

§ 371 (c)(1),
(2), (4) Date: Jan. 10, 2008

(87) PCT Pub. No.: WO2007/006531

PCT Pub. Date: Jan. 18, 2007

(65) Prior Publication Data

US 2008/0234490 A1   Sep. 25, 2008

(30) Foreign Application Priority Data

Jul. 11, 2005 (GB) .................................. 0514206.2

(51) Int. Cl.
*A61K 31/41* (2006.01)
*C07D 403/00* (2006.01)
(52) U.S. Cl. ...................................... 514/381; 548/250
(58) Field of Classification Search ................. 514/381; 548/250
See application file for complete search history.

(56) References Cited

U.S. PATENT DOCUMENTS

| 5,371,233 A | * | 12/1994 | Daumas et al. | ............. 548/250 |
| 2007/0043098 A1 | * | 2/2007 | Sedelmeier | ................. 514/381 |

FOREIGN PATENT DOCUMENTS

| EP | 1878729 | 1/2008 |
| EP | 1533305 | 2/2008 |
| WO | WO 2004/026847 | 4/2004 |
| WO | WO 2005/014602 | 5/2005 |

* cited by examiner

*Primary Examiner*—Susannah Chung
(74) *Attorney, Agent, or Firm*—Joseph T. Majka

(57) ABSTRACT

The invention relates to a method or process for the manufacture of blood pressure lowering agents, such as valsartan, novel intermediates as well as process steps in said synthesis. The method or process leads via the novel intermediate salts of the formula IA,

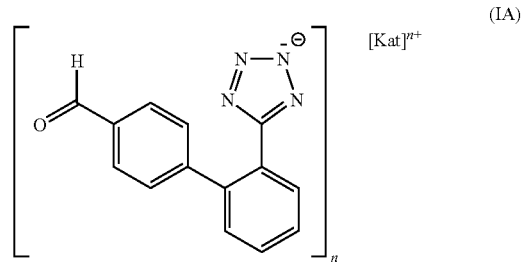

(IA)

or a tautomer thereof, wherein $[kat]^{n+}$ is a cation and n is 1, 2, 3, 4, 5 or 6.

14 Claims, No Drawings

METAL SALTS OF 2'-(1H-TETRAZOL-5YL)-1.1'-BIPHENYL-4-CARBOXALDEHYDE

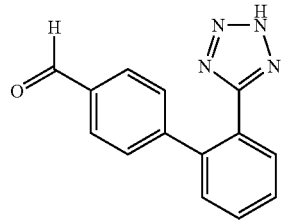

(I)

SUMMARY OF THE INVENTION

The invention relates to a method or process for the manufacture of blood pressure lowering agents, such as valsartan, novel intermediates as well as process steps in said synthesis.

BACKGROUND OF THE INVENTION

The enzyme angiotensin converting enzyme (ACE) catalyses the hydrolysis of the deca-peptide Angiotensin I to the octapeptide Angiotensin II. The latter contributes to a number of physiological mechanisms that lead to the elevation of blood pressure. Many of these mechanisms are initialized by the binding of Angiotensin II to the Angiotensin receptor $AT_1$.

A number of inhibitors of the binding of Angiotensin II to this receptor are known—for example valsartan, losartan, irbestan, candesartan cilexetil, tasosartan, telmisartan, eprosartan, zolasartan and saprisartan. By blocking of the binding and thus the activation of the $AT_1$ receptor, these active compounds are able to lower blood pressure. These and other comparable compounds are therefore commonly referred to as angiotensin II receptor antagonists or more recently as angiotensin receptor blockers (ARBs).

Except for telmisartan, eprosartan and saprisartan, the mentioned compounds share a common structural feature in the form of a pharmacophore of the following partial formula A,

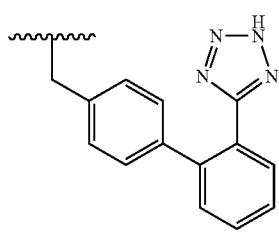

(A)

where the waved line indicates the place of binding to the rest of the molecule (which may also be present in tautomeric form, either in equilibrium or totally, with the hydrogen at the tetrazolyl ring at the 1-instead of the 2-position of that ring; the same also is true for any compound mentioned below where such tautomerism is possible and will therefore not be mentioned specifically in any case).

PCT application WO 05/014602 A1 describes a process for the manufacture of intermediates useful in the synthesis of this common moiety and the final pharmaceutically active compounds, such as the ARBs mentioned above, e.g. valsartan. There, the synthesis of an aldehyde of the formula I, is described which is further reacted to various pharmaceutically active substances such as the ARBs, e.g. valsartan, directly or via one or more further reaction steps and intermediates.

In a reaction described in WO 2005/014602, the crude product of the formula I obtainable after oxidation of the hydroxymethyl precursor to the aldehyde of the formula I is used in a subsequent reductive amination, for example, with L-valine.

When the aldehyde of the formula I is produced and used in the subsequent reaction step, this, in the case of production in industrial scale, comprises a significant amount of water, that is, up to now it has been regarded as convenient to use said aldehyde in "wet" form.

A problem to be solved by the present invention is to find a yet improved process and/or intermediates that allow for an improved process of manufacture of ARBs, especially valsartan, that is especially useful for manufacturing processes in an industrial scale.

GENERAL DESCRIPTION OF THE INVENTION

It has now been found surprisingly that the process can be led still more advantageously by using salts of the aldehyde of the formula I that much more conveniently allow to use the aldehyde in dry form. This allows an improved production in large industry scale and even better handling in this manufacturing process. The use of salts of the compound of the formula I makes it possible to manufacture pharmaceuticals comprising a pharmacophore of the formula A shown above by a process according to the invention which comprises the manufacture of an intermediate of the formula I as anion with a cation and thus in the form of a salt, especially of the formula IA shown below.

Such salts are very stable, can be dried very conveniently and their use in dry form in the subsequent step allows for a very well defined process, leading to very low amounts of impurities such as starting materials in the subsequent intermediates and thus facilitating the use of these subsequent intermediates in the synthesis of the final products.

The salts of an aldehyde of the formula I can be dried, handled, stored, transported, processed and/or reacted in large amounts. They allow for subsequent reactions, e.g. by reductive amination as described above and below, an improved yield and/or quality of the obtainable consecutive product, thus facilitating an economic and (as less byproducts and thus less waste and energy (e.g. for workup) are required) ecologically improved process design. Thus they contribute to a safe and advantageous process.

DETAILED DESCRIPTION OF THE INVENTION

The invention relates to a process or method for the manufacture of a salt of an aldehyde of the formula IA,

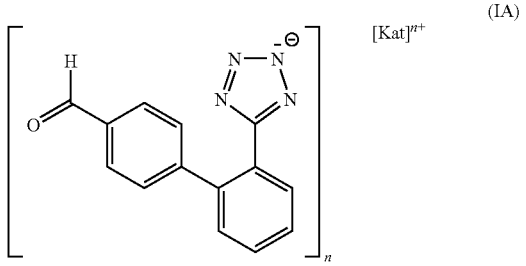

or a tautomer thereof, wherein [Kat]$^{n+}$ is a cation and n is 1, 2, 3, 4, 5 or 6, preferably 1, 2 or 3, comprising forming and isolating said salt from a solution comprising a compound of the formula I as shown above and a cation providing material.

[Kat]$^{n+}$ is preferably a cation selected from at least one of alkali metal cations, such as lithium, sodium, potassium, rubidium or cesium (n=1), earth alkali metal cations, such as magnesium, calcium, strontium or barium (n=2), aluminium cations, indium cations and gallium cations, a cation from other metals from the periodic table of elements, such as molybdenum, tungsten, manganese, iron, cobalt, nickel, copper, zinc, and unsubstituted or substituted ammonium cations, e.g. the ammonium ion, substituted ammonium cations, such as mono-, di-, tri- or preferably tetrasubstituted ammonium cations where the substitutents are preferably organic moieties bound via a carbon atom and may, for example, be selected from alkyl, such as $C_1$-$C_{20}$-alkyl, aryl, such as mono-, bi- or tricyclic aryl with 6 to 20 ring atoms, aryl-alkyl, wherein aryl and alkyl are preferably as just defined, cycloalkyl, such as $C_3$-$C_{12}$-cycloalkyl, cycloalkyl-alkyl, wherein cycloalkyl and alkyl are preferably as just defined, heterocyclyl wherein heterocyclyl preferably is an unsaturated, partially saturated or fully saturated mono-, bi- or tricyclic ring having 3 to 20 ring atoms and at least one, preferably up to three, ring atoms are heteroatoms independently selected from nitrogen or preferably oxygen or sulfur, heterocyclyl-alkyl wherein heterocyclyl and alkyl are preferably as just defined, or the ammonium nitrogen may be part of a ring, e.g. as part of a heterocycle, e.g. an unsaturated, partially saturated or fully saturated mono-, bi- or tricyclic ring having 3 to 20 ring atoms wherein at least one, preferably up to three, ring atoms are hetero atoms independently selected from nitrogen, oxygen or sulfur, with the proviso that at least one ring nitrogen is present.

A cation providing material can be any type of salt or a cation exchanger resin; preferred as a salt is a basic salt of a metal (especially one forming a cation [Kat]$^{n+}$ as described as preferred above) or unsubstituted or substituted ammonium cation (especially as described for a cation [Kat]$^{n+}$ as preferred above), especially an acid addition salt of a weak organic or inorganic acid, e.g. of a carbonic acid, a phosphate or especially a carbonate, or more preferably a hydroxide or alcoholate salt. As anion in an alcoholate salt, the anion of an aromatic, alicyclic, aromatic-aliphatic, alicyclic-aliphatic or preferably an aliphatic alcohol, each of which may preferably have up to 20, more preferably up to 7 carbon atoms, e.g. the anion of an alkyl alcohol with up to 20, preferably up to seven carbon atoms, more preferably e.g. the anion of methanol or ethanol, are preferred. A cation providing material may also be a metal that is capable of reacting with the tetrazolyl proton, such as lithium, sodium or potassium, or a metal hydride, such as lithium hydride, sodium hydride, calcium hydride or aluminium hydride.

A solution comprising a compound of the formula I as shown above and a cation providing material comprises at least one solvent, more preferably an organic solvent.

The formation of the salt of the formula IA preferably takes place by dissolving a compound of the formula I and a cation forming material in one or more solvents or diluents that dissolve them, may take place at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under vacuum, e.g. for concentrating the solution by removal of solvent, or and/or in an inert atmosphere, for example under an argon or nitrogen atmosphere.

During the dissolving, in addition to a dissociation of cation and anion a cation forming material may change partially or completely—for example, in an aqueous solution, addition of an alcoholate of a cation may result in the formation of the alcohol and hydroxyl anions. Preferably, the solvent is chosen so that no such reaction takes place.

The solvents may be selected include those mentioned specifically (e.g. in the Examples) or, for example, water, or preferably organic solvents, for example esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as toluene or xylene, nitriles, such as acetonitrile, halogenated hydro-carbons, e.g. chlorobenzene, methylene chloride, 1,2-dichloroethane or chloroform, acid amides, such as dimethylformamide or dimethyl acetamide, cyclic, linear or branched hydrocarbons, such as cyclohexane, hexane or isopentane, or preferably alcohols, such as methanol, ethanol or 1- or 2-propanol, or mixtures of two or more such solvents. Such solvents or solvent mixtures may also be used in working up.

The reaction to and formation of the salt may take place directly in the solution, resulting e.g. in the precipitation of a salt of the formula IA, and/or it may take place during the isolation, e.g. during evaporation or the like, or both (e.g. during concentration to a smaller volume).

The isolation of a salt of the formula can be carried out under reaction conditions that are known per se and may follow customary procedures and steps, e.g. selected from the group comprising but not limited to distribution (e.g. extraction), neutralization, crystallization, re-crystallization, digestion, chromatography, evaporation, drying, filtration, washing, centrifugation and the like. Most preferred are partial or complete evaporation of one or more solvents present, the addition of less polar solvents to a mixture with more polar solvents (e.g. the addition of an ether, such as diethyl ether or tert-butylmethyl ether, to an alcohol, such as methanol or ethanol), and/or crystallization (with or without addition of seed crystals).

It is also possible to combine two or more isolation steps, e.g. in order to obtain a more pure salt of the formula IA. For example, a first isolation step may be followed by re-crystallization from an appropriate solvent, e.g. an alcohol, such as isopropanol.

The invention also relates to a salt of the formula IA as given above as such, or a tautomer thereof.

The salt of a compound of the formula I is, in formula IA, mainly represented to display its stoichiometry and not intended to represent the structure in detail. Thus, formula IA does not exclude the possibility that different tautomeric forms of a compound of the formula are present (either in equilibrium or alone), such as a form with the formula IA*:

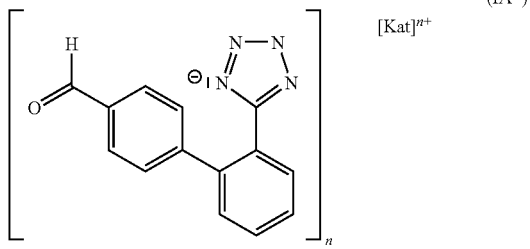

(IA*)

A salt of the formula IA may further include trace amounts of customary impurities, in addition certain amounts of a solvent (preferably other than water) (bound as solvate and/or in other form), of the free compound of the formula I and/or the cation providing material may be present, e.g. up to 20%, preferably up to 5%. More preferably, the salt of the formula IA is isolated in substantially pure form.

The invention also relates to the use of a salt of the formula IA in the process for the manufacture or a pharmaceutical, especially an ARB, most especially valsartan, as well as a corresponding process or method.

The corresponding reaction steps can be derived from the general description or from the examples in WO 2005/014602 which, in this regard, especially with regard to the manufacture of valsartan (either in the examples or in the general description) is incorporated by reference herewith.

For example, in the production of valsartan, or a salt thereof, a) a salt of the formula IA can be reacted with a valine derivative of the formula IV,

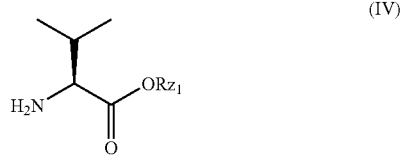

(IV)

or a salt thereof, wherein $Rz_1$ is hydrogen or a carboxy protecting group, under conditions of reductive amination;

b) followed by acylating a resulting compound of the formula (V),

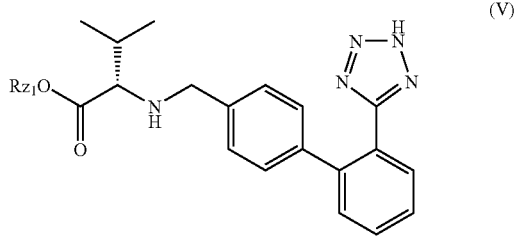

(V)

wherein $Rz_1$ is as defined for a compound of the formula IV, or a salt thereof, with a compound of the formula VI

(VI)

wherein $Rz_2$ is an activating group;
and removing any protecting group(s) present;
whereby a compound of the formula VII

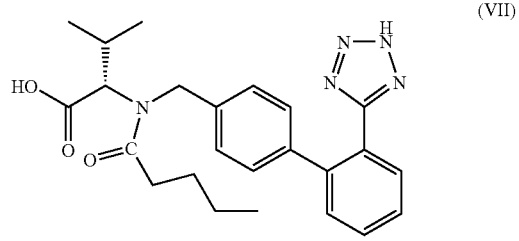

(VII)

(valsartan=(S)-3-methyl-2-{pentanoyl-[2'-(1H-tetrazol-5-yl)biphenyl-4-yl-methyl]-amino}-butyric acid) and/or a tautomer thereof, or a salt thereof (e.g. an earth alkali metal salt, such as the magnesium or calcium salt, see US 2005/0101652 which is incorporated herein by reference especially with regard to the salt formation and the salts of valsartan), is obtained;

and, if desired, converting a free compound of the formula VII into a salt thereof or a salt into the free compound or a different salt thereof.

The reductive amination under a) is carried out in the presence of a reducing agent. A suitable reducing agent is for example a borohydride or hydrogen or a hydrogen donor both in the presence of a hydrogenation catalyst, or a suitable selenide or silane.

The reductive amination takes place in two steps via the corresponding aldimine (Schiff Base) and its subsequent reduction, and it is possible to form first the aldimine, isolate it and then reduce it to a compound of the formula V, or salt thereof, or to perform both the aldimine formation and the reduction without isolation of the aldimine.

Suitable conditions and material, e.g. reducing agents, such as those mentioned above, the corresponding reaction conditions, such as solvents and appropriate temperatures, as well as suitable protecting groups $Rz_1$ are preferably as described in WO 05/014602 which, in this regard, is incorporated herewith by reference.

The acylation under b) preferably takes place in the presence of a suitable base.

Suitable conditions and materials, e.g. suitable bases, suitable reaction conditions, such as solvents and appropriate temperatures, as well as suitable activating groups $Rz_2$ are preferably as described in WO 05/014602 which, especially in this regard, is incorporated herewith by reference.

The removal of (a) protecting group(s) may take place under conditions known in the art. For example, the removal may take place as described in J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosauren, Peptide, Proteine" (*Amino* acids, *Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage). Different protecting groups can be selected so that they can be removed selectively at different steps while other protecting groups remain intact. The corresponding alternatives can be selected readily by the person skilled in the art from those given in the standard reference works mentioned above or the description or especially as described in WO 05/014602, which is incorporated herewith, especially with regard to the removal of protecting groups (especially $Rz_1$), by reference.

An activating group $Rz_2$ may, for example, be an activating group that is used in the field of peptide chemistry, such as halo, e.g. chloro, fluoro or bromo, $C_1$-$C_7$-alkylthio, e.g. methylthio, ethylthio or tert-butyl-thio; pyridylthio such as 2-pyridylthio; imidazolyl such as 1-imidazolyl; benzthiazolyloxy, such as benzthiazolyl-2-oxy; benzotriazolyl-oxy such as benzotriazolyl-1-oxy; $C_2$-$C_8$-alkanoyloxy, such as butyroyloxy or pivaloyloxy; or 2,5-dioxo-pyrrolidinyl-1-oxy; the activation may also take place in situ using customary activation reagents in the presence of a free acid corresponding to the compound of the formula VI.

In one preferred embodiment, a reaction according to the invention, either leading to a salt of the formula IA or to a pharmaceutical, in addition comprises a reaction step that leads to a compound of the formula I which may then be isolated in crude form and/or directly reacted according to the invention forming and isolating a salt of the formula IA.

For example, a compound of the formula I may be obtained by oxidizing a hydroxymethyl compound of the formula II,

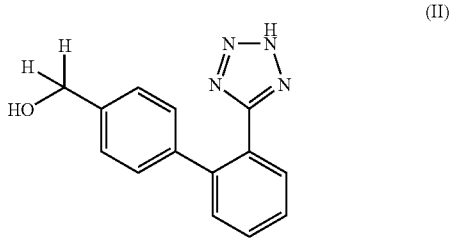

(II)

or a salt thereof to a compound of the formula I which may then, in the same reaction vessel or after isolation of the crude material, be reacted according to the present invention to a salt of the formula IA. The oxidation takes place in the presence of a suitable oxidizing agent, for example, an alkali metal (such as lithium, sodium or potassium) hypochlorite, a "TEMPO" or an analogue or an oxidizing agent selected from the group consisting of $HNO_2$, $HNO_3$ or anhydrides thereof, and peroxidisulfates, in appropriate solvents and at appropriate temperatures, e.g. as described in WO 05/014602. A salt of a compound of the formula II may be a salt of the corresponding anion with a metal cation $[Kat]^{n+}$ as described for a salt of the formula IA. Such a salt of a compound of the formula II also forms an embodiment of the present invention. It can be manufactured analogously to a salt of a compound of the formula IA by methods such as those described above or below.

A compound of the formula II can preferably be obtained by reacting a cyanide of the formula II,

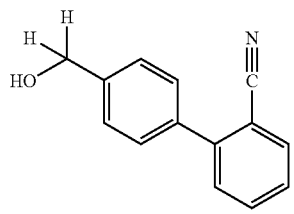

with an azide of the formula $(R_1)(R_2)$-M-$N_3$ wherein $R_1$ and $R_2$ represent, independently of each other, an organic residue, especially $C_1$-$C_8$-alkyl, such as methyl, ethyl, n-propyl, i-propyl, isobutyl, tert-butyl or n-octyl; $C_3$-$C_7$alkenyl, such as allyl or crotyl; $C_3$-$C_7$-cycloalkyl, such as cyclohexyl; phenyl-$C_1$-$C_4$-alkyl, such as benzyl or 2-phenethyl; phenyl-$C_2$-$C_5$-alkenyl, such as cinnamyl; $C_3$-$C_8$-cycloalkyl-$C_1$-$C_8$-alkyl, such as cyclopropylmethyl or cyclo-hexylmethyl; or phenyl-$C_2$-$C_5$alkenyl; and M is boron or aluminium. This [2+3] cycloaddition yields a compound of the formula II, or a salt thereof which can also be formed from the free compound by analogous methods as those described for the formation of a salt of the formula IA.

Preferred meanings for $R_1$, $R_2$ and M, as well as preferred reaction conditions, such as molar ratios, solvents and reaction temperatures, can be derived from WO 05/014602, which, preferably in this regard, is incorporated herewith by reference.

Preferably, the formation of the tetrazole ring to obtain a compound of the formula II, or a salt thereof, and the oxidation to a compound of the formula I take place in sequence in one reaction vessel.

All reaction steps, except those for the manufacture of a salt of the formula IA, as well as preferred reaction conditions for these reaction steps, can also be derived from the general description or from the examples in WO 2005/014602 which, preferably in this regard, is incorporated by reference herewith.

Where the term "lower" is used for the description of moieties, e.g. "lower alkyl", this is intended to mean that the corresponding moiety preferably has up to seven, more preferably up to four carbon atoms. Alkyl, such as lower alkyl, $C_1$-$C_6$-alkyl or $C_1$-$C_7$alkyl, may be linear or branched one or more times.

The invention preferably relates to the embodiments defined by the claims attached below which are therefore incorporated into the present description here by reference. In the claims, more general expressions or reaction steps may be replaced, individually, in groups of two or more or all in each claim, by the more specific (e.g. preferred) expressions or reaction steps described in the description or subclaims, thus yielding more preferred embodiment of the respective invention embodiments.

The following Examples, while themselves also providing preferred embodiments of the salts and the methods or processes of manufacture according to the invention, serve to illustrate the invention without limiting the scope of it.

Example 1

2'-(1H-Tetrazol-5-yl)-1,1'-biphenyl-4-carboxaldehyde potassium salt and its manufacture 2.50 g of 2'-(1H-Tetrazol-5-yl)-1,1'-biphenyl-4-carboxaldehyde ("biphenyl tetrazol aldehyde" hereinafter) are dissolved in 25 ml of methanol at room temperature. 1.12 g of potassium hydroxide are added to the solution over a period of 30 minutes (min) at room temperature under stirring. After 30 min of stirring at 20-22° C., the solution is evaporated and the off white solid is dried under vacuum at 40° C. to give the title salt.

NMR: 1H (d6-DMSO) in accordance with the structure. Melting point: above 235° C.

Example 2

2'-(1H-Tetrazol-5-yl)-1,1'-biphenyl-4-carboxaldehyde sodium salt and its manufacture 10 g (40 mmol) of "biphenyl tetrazol aldehyde" are dissolved in 50 ml of methanol at room temperature. 1.6 g (40 mmol) of sodium hydroxide are added to the solution over a period of 30 min at room temperature and under stirring. After 30 min of stirring at 20-22° C., the solution is evaporated and the solid is dried under vacuum at 40° C. This white solid is then taken up an crystallized from isopropanol. The suspension is cooled down to 0° C. and allowed to stand at this temperature for 24 h. After filtration, the filter cake is washed with cold isopropanol and dried under vacuum at 40° C. to give the title salt.

NMR: 1H (d6-DMSO) in accordance with the structure. Melting point: degradation up to 165° C.

Example 3

2'-(1H-Tetrazol-5-yl)-1,1'-biphenyl-4-carboxaldehyde sodium salt and its manufacture from sodium methylate 30% in methanol 20 g (80 mmol) of "biphenyl tetrazol aldehyde" are dissolved in 25 ml of methanol at room temperature. 14.4 g of sodium methylate (80 mmol) are added to the solution over a period of 30 min and at room temperature. After 10 min of stirring at 20-22° C., the solution is heated to 45° C. 160 ml of tert-butyl methylether (TBME) are added over a period of 30 min to the solution of tetrazoyl-biphenyl-aldehyde salt. The solution is allowed to cool down to room temperature. After 12 hours of stirring at 20-22° C., the suspension is diluted with 50 ml of TBME, cooled down to 0° C. and allowed to stir at this temperature for 4 h. After filtration, the filter cake is washed with cold TBME and dried under vacuum at 40° C. to give the title salt.

The properties of the salt correspond to those given in Example 2.

Example 4

2'-(1H-Tetrazol-5-yl)-1,1'-biphenyl-4-carboxaldehyde lithium salt and its manufacture 5.0 g (20 mmol) of "biphenyl tetrazol aldehyde" are dissolved in 25 ml of methanol at room temperature. 0.48 g (20 mmol) of lithium hydroxide are added to the solution over 5 min at room temperature. After 30 min of stirring at 20-22° C., the solution is evaporated and the solid is dried under vacuum at 40° C. This white solid is re-crystallized from isopropanol. The suspension is cooled down to 0° C. and allowed to stand at this temperature for 24 h. After filtration, the filter cake is washed with cold isopropanol and dried under vacuum at 40° C. to give the title salt.

NMR: 1H (d6-DMSO) in accordance with the structure. Melting point: higher than 235° C.

Example 5

2'-(1H-Tetrazol-5-yl)1,1'-biphenyl-4-carboxaldehyde sodium salt and its manufacture in methanol with sodium methylate (medium scale)

75 g (300 mmol) of "biphenyl tetrazol aldehyde" are dissolved in 75 ml of methanol at room temperature. 54.02 g of sodium methylate 30% (300 mmol) are added to the solution under stirring over a period of 30 minutes and at room temperature. After 10 min of stirring at 20-22° C., the solution is heated to 45° C. 500 ml TBME are added over 30 min to the solution of tetrazolyl-biphenyl-aldehyde salt. The solution is then allowed to cool down to room temperature. After 12 hours stirring at 20-22° C. the suspension is filtered. After filtration, the filter cake is washed with cold TBME and dried under vacuum at 40° C. to give 86.15 g off white power.

For some of the above mentioned salts DSC measurements are performed that show the high stability of the salts of the formula IA.

The invention claimed is:

1. A process or method for the manufacture of a salt of an aldehyde of the formula IA,

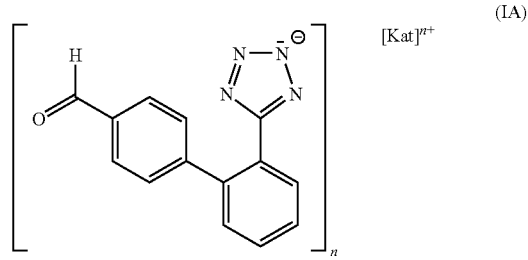

or a tautomer thereof, wherein [Kat]$^{n+}$ is a cation and n is 1, 2, 3, 4, 5 or 6, comprising forming and isolating said salt from a solution comprising a compound of the formula I

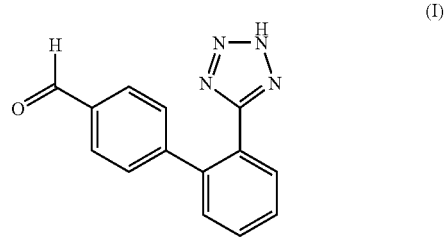

and a cation providing material.

2. The process or method according to claim 1, wherein in formula IA [Kat]$^{n+}$ is a cation selected from the group consisting of at least one of alkali metal cations with n=1, earth alkali metal cations with n=2, aluminium cations with n=3, molybdenum, tungsten, manganese, iron, cobalt, nickel, copper, zinc, and unsubstituted or substituted ammonium cations, e.g. the ammonium ion or substituted ammonium cations, especially mono-, di-, tri- or preferably tetrasubstituted ammonium cations where the substitutents are preferably organic moieties bound via a carbon atom and may, for example, be selected from the group consisting of alkyl, such as $C_1$-$C_{20}$-alkyl, aryl, such as mono-, bi- or tricyclic aryl with 6 to 20 ring atoms, aryl-alkyl, wherein aryl and alkyl are preferably as just defined, cycloalkyl, such as $C_3$-$C_{12}$-cycloalkyl, cycloalkyl-alkyl, wherein cycloalkyl and alkyl are preferably as just defined, heterocyclyl wherein heterocyclyl preferably is an unsaturated, partially saturated or fully saturated mono-, bi- or tricyclic ring having 3 to 20 ring atoms and at least one, for example up to three, ring atoms are heteroatoms independently selected from nitrogen or preferably oxygen or sulfur, and heterocyclyl-alkyl wherein heterocyclyl and alkyl are preferably as just defined, or the ammonium nitrogen may be part of a ring, e.g. as part of a heterocycle, e.g. an unsaturated, partially saturated or fully saturated mono-, bi- or tricyclic ring having 3 to 20 ring atoms wherein at least one, preferably up to three, ring atoms are heteroatoms independently selected from nitrogen, oxygen or sulfur, with the proviso that at least one ring nitrogen is present.

3. The process or method according to claim 1, wherein the cation providing material is a salt, a metal, a metal hydride or a cation exchanger resin.

4. The process or method according to claim 3, wherein the salt is a basic salt of a metal or an unsubstituted or substituted ammonium cation, preferably with a metal or cation as described for [Kat]$^{n+}$ in formula IA, especially an acid addition salt of a weak organic or inorganic acid, e.g. of a carbonic acid, a phosphate or especially a carbonate, or more preferably a hydroxide or alcoholate salt, where as an alcoholate salt, the anion of an aromatic, alicyclic, aromatic-aliphatic, alicyclic-aliphatic or preferably an aliphatic alcohol, each of which may preferably have up to 20, more preferably up to 7 carbon atoms, e.g. the anion of an alkyl alcohol with up to 20, preferably up to seven carbon atoms, more preferably e.g. the anion of methanol or ethanol, is preferred.

5. The process or method according to claim 1 wherein forming or formation of a salt of the formula IA takes place by dissolving a compound of the formula I,

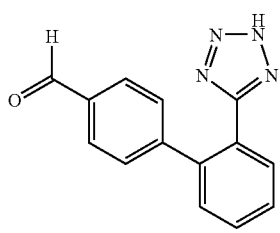

and a cation forming material, especially the cation forming material according to any one of claims 3 or 4, in one or more solvents or diluents and isolating of a salt of the formula IA follows, especially by distribution, neutralization, crystallization, re-crystallization, digestion, chromatography, evaporation, drying, filtration, washing, centrifugation or a combination of two or more of these methods.

6. A salt of the formula IA,

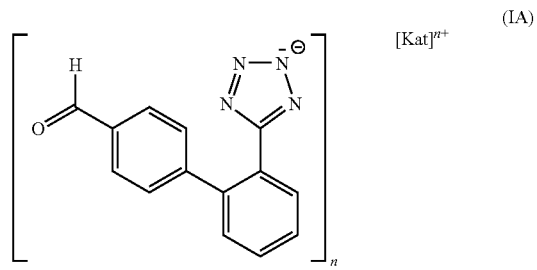

or a tautomer thereof, wherein [Kat]$^{n+}$ is a cation and n is 1, 2, 3, 4, 5 or 6.

7. A salt of the formula IA according to claim 6 wherein [Kat]$^{n+}$ is an alkali metal cation, such as lithium, sodium, potassium, rubidium or cesium (n=1), an earth alkali metal cation, such as magnesium, calcium, strontium or barium (n=2), aluminium, indium or gallium; a zinc or an unsubstituted or substituted ammonium cation, especially as defined in claim 2.

8. A salt of the formula IA according to claim 6 selected from the group consisting of salts with the following names:
  2'-(1H-tetrazol-5-yl)-1,1'-biphenyl-4-carboxaldehyde potassium salt,
  2-(1H-tetrazol-5-yl)-1,1-biphenyl-4-carboxaldehyde sodium salt and
  2-(1H-tetrazol-5-yl)-1,1'-biphenyl-4-carboxaldehyde lithium salt.

9. The process according to claim 1, further comprising manufacturing a compound of the formula I as given in claim 5 by oxidizing a hydroxymethyl compound of the formula II,

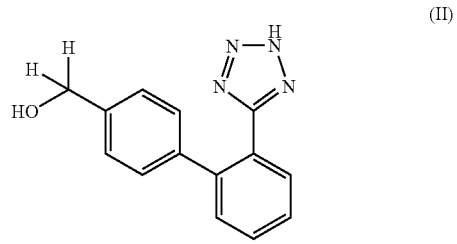

or a salt thereof to a compound of the formula I which may then, in the same reaction vessel or after isolation of the crude material, be reacted according to the present invention to a salt of the formula IA.

10. The process according to claim 9, further comprising forming a compound of the formula II as given in claim 9 by reacting a cyanide of the formula III,

with an azide of the formula $(R_1)(R_2)$-M-N3 wherein $R_1$ and $R_2$ represent, independently of each other, an organic residue, especially $C_1$-$C_8$-alkyl, such as methyl, ethyl, n-propyl, isopropyl, isobutyl, tert-butyl or n-octyl; $C_3$-$C_7$-alkenyl, such as allyl or crotyl; $C_3$-$C_7$-cycloalkyl, such as cyclohexyl; phenyl-$C_1$-$C_4$-alkyl, such as benzyl or 2-phenethyl; phenyl-$C_2$-$C_5$-alkenyl, such as cinnamyl; $C_3$-$C_8$-cycloalkyl-$C_1$-$C_8$-alkyl, such as cyclopropylmethyl or cyclohexylmethyl; or phenyl-$C_2$-$C_5$alkenyl; and M is boron or aluminium.

11. A process or method for the manufacture of a pharmaceutical, comprising the use of a salt of the formula IA as defined in claim 1.

12. The process or method according to claim 11, wherein the pharmaceutical is an angiotensin receptor blocker, preferably valsartan.

13. The process or method according to claim 11, comprising the use of a salt of the formula IA obtained according to a method or process as described in any one of claim 1 more preferably obtained according to claim 9, most preferably according to claim 10.

14. The process of method according to claim 11, for the production of valsartan or the formula VII

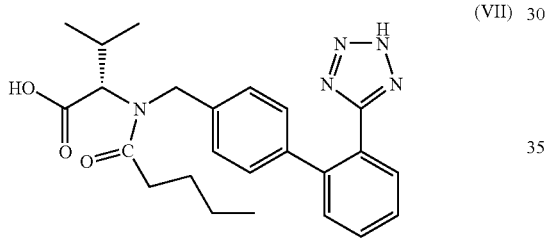 (VII)

or a salt thereof, comprising a) reacting a salt of the formula IA with a valine derivative of the formula IV,

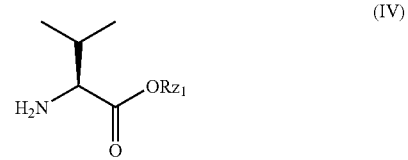 (IV)

or a salt thereof, wherein $Rz_1$ is hydrogen or a carboxy protecting group, under conditions of reductive amination;

b) acylating a resulting compound of the formula (V),

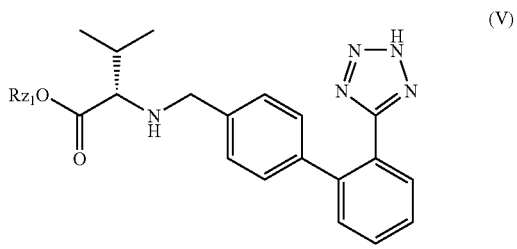 (V)

wherein $Rz_1$ is as defined for a compound of the formula IV, or a salt thereof, with a compound of the formula VI

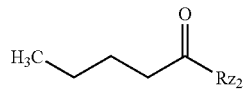 (VI)

wherein $Rz_2$ is an activating group;
and removing any protecting group(s) present.

* * * * *